(12) United States Patent
Mustad et al.

(10) Patent No.: US 7,759,507 B2
(45) Date of Patent: Jul. 20, 2010

(54) LIPID SYSTEM AND METHODS OF USE

(75) Inventors: Vikkie A. Mustad, Galena, OH (US); Stephen DeMichele, Dublin, OH (US); Bradley A. Zinker, Vernon Hills, IL (US); Yung-Sheng Huang, Upper Arlington, OH (US)

(73) Assignee: Abbott Laboratories, Abbott Park, IL (US)

( * ) Notice: Subject to any disclaimer, the term of this patent is extended or adjusted under 35 U.S.C. 154(b) by 113 days.

(21) Appl. No.: 10/656,662

(22) Filed: Sep. 5, 2003

(65) Prior Publication Data

US 2005/0054724 A1    Mar. 10, 2005

(51) Int. Cl.
A23D 9/00 (2006.01)

(52) U.S. Cl. .................. 554/224; 554/227; 514/547; 426/301

(58) Field of Classification Search .................. 554/224, 554/227; 426/301; 514/547
See application file for complete search history.

(56) References Cited

U.S. PATENT DOCUMENTS

| | | | |
|---|---|---|---|
| 4,526,902 A | 7/1985 | Rubin | |
| 4,921,877 A | 5/1990 | Cashmere et al. | |
| 5,059,622 A | 10/1991 | Sears | |
| 5,308,832 A | 5/1994 | Garleb et al. | |
| 5,502,077 A | 3/1996 | Breivik et al. | |
| 5,656,667 A | 8/1997 | Breivik et al. | |
| 5,698,594 A | 12/1997 | Breivik et al. | |
| 5,763,484 A | 6/1998 | Horrobin | |
| 5,780,451 A | 7/1998 | DeMichele et al. | |
| 5,895,652 A | 4/1999 | Giampapa | |
| 5,922,345 A | 7/1999 | Horrobin et al. | |
| 5,922,704 A | 7/1999 | Bland | |

(Continued)

FOREIGN PATENT DOCUMENTS

CN    1339262    3/2002

(Continued)

OTHER PUBLICATIONS

Kato et al., Effect of Alpha-Linolenic Acid on Blood Glucose, Insulin and GLUT4 Protein Content of Type 2 Diabetic Mice, *Journal of Health Science* 46, 489-492 (2000).

(Continued)

*Primary Examiner*—Deborah D Carr
(74) *Attorney, Agent, or Firm*—William J. Winter; Sandra E. Weids; Vincent S. Egolf

(57) ABSTRACT

The present invention relates to a lipid system, and methods for using such a lipid system, containing specific relative ratios of omega-3, omega-6, and omega-9 fatty acids. The lipid system may be used independently or as a component of a nutritional product. A lipid system according to the present invention may contain omega-3 fatty acids, omega-6 fatty acids, and omega-9 fatty acids with the ratio of omega-6 fatty acids to omega-3 fatty acids preferably being between 0.25:1 and 3:1, and the ratio of omega-9 fatty acids to omega-3 fatty acids preferably being between 0.4:1 and 3:1. The present invention also relates to methods for administering a lipid system or a nutritional product containing the lipid system to an individual.

22 Claims, 4 Drawing Sheets

* = SIGNIFICANTLY DIFFERENT vs MUFA CONTROL BLEND, P<0.05.

U.S. PATENT DOCUMENTS

| | | | |
|---|---|---|---|
| 5,952,314 | A | 9/1999 | DeMichele et al. |
| 6,140,304 | A | 10/2000 | Sears |
| 6,468,987 | B1 | 10/2002 | DeMichele et al. |
| 2004/0062847 | A1* | 4/2004 | Koike et al. ............. 426/601 |

FOREIGN PATENT DOCUMENTS

| | | |
|---|---|---|
| EP | 0937408 | 8/1993 |
| EP | 0682879 | 11/1995 |
| EP | 1269859 | 1/2003 |
| GB | 2223943 | 3/1990 |
| JP | 8198749 | 8/1996 |
| WO | WO 9526646 | 10/1995 |
| WO | WO 99/62359 | 12/1999 |
| WO | WO 0112179 | 2/2001 |
| WO | WO 0211552 | 2/2002 |
| WO | WO 0217903 | 3/2002 |

OTHER PUBLICATIONS

Hun et al., Increased Uncoupling Protein2 mRNA in White Adepose Tissue, and Decrease in Leptin, Visceral Fat, Blood Glucose, and Cholesterol in KK-A$^y$ Mice Fed with Eicosapentaenoic and Docohexanoic Acids in Addition to Linolenic Acid, *Biochemical and Biophysical Research Communications* 259, 85-90 (1999).

McManus et al., A Comparison of the Effects of n-3 Fatty Acids from Linseed Oil and Fish Oil in Well-Controlled Type II Diabetes, *Diabetes Care* 19, 463-467 (1996).

Goh et al., Effect of ω3 Fatty Acid on Plasma Lipids, Cholesterol and Lipoprotein Fatty Acid Content in NIDDM Patients, *Diabetologia* 40, 45-52 (1997).

Nestel et al., Aterial Compliance in Obese Subjects is Improved with Dietary Plant n-3 Fatty Acid from Flaxseed Oil Despite Increased LDL Oxidizability, *Arteriosclerosis, Thrombosis, and Vascular Biology* 17, 1163-1170 (1996).

Simopoulos, Essential Fatty Acids in Health and Chronic Disease, *Am. J. Clin. Nutr.* 70 (suppl.), 560S-569S (1999).

Siguel, Deficiencies and Abnormalities of Essential Fats in Gastrointestinal and Corinary Artery Disease, *J. Clin. Ligand Assay* 23, 104-111 (2000).

\* cited by examiner

LIPID SYSTEM AND METHODS OF USE

FIELD OF THE INVENTION

The present invention relates to a lipid system containing specific ratios of omega-3, omega-6, and omega-9 fatty acids and methods for using such a lipid system. The lipid system disclosed is suitable for independent use or as a component of a nutritional product.

BACKGROUND

Blood glucose control is a primary goal when treating individuals with type 2 diabetes. Glucose control alone, however, does not eliminate a diabetic's risk for vascular complications or vascular diseases. Vascular complications and vascular diseases impair the ability of the arteries in the circulatory system in general and the coronary arteries in particular to expand (vasodilate) and contract (vasoconstrict). Vascular complications represent the most severe manifestations of type 2 diabetes. For example atherosclerosis of the coronary, cerebral, and peripheral arteries is 24 times more prevalent in individuals with diabetes compared to non-diabetics and these conditions occur earlier and progress more rapidly in diabetics. The primary vascular complications of a diabetic include an increased incidence of lower limb ischema and neuropathy (which can lead to amputation), kidney disease, heart attack, and retinopathy (which can lead to blindness). In addition, when individuals with diabetes develop clinical vascular disease, they sustain a worse prognosis for survival than do individuals without diabetes. Although dietary control of blood glucose is a primary goal for individuals with diabetes, glucose control alone does not completely offset the increased risk for vascular disease.

The underlying metabolic cause of type 2 diabetes is the combination of impairment in insulin-mediated glucose disposal (insulin resistance) and/or defective secretion of insulin by pancreatic cells, i.e., people with type 2 diabetes no longer use or secrete insulin properly. The accelerated development of the vascular complications in type 2 diabetics is the result of a combination of insulin resistance and the non-random clustering of risk factors that accompany insulin resistance. These risk factors include hypertension (up to 75% of vascular disease occurs in diabetic individuals with hypertension), increased levels of more atherogenic lipoproteins (small dense LDL and triglyceride-rich lipoproteins), low levels of HDL cholesterol, and elevated levels of hemostatic (blood clotting) factors and C-reactive protein (a marker of inflammation). Collectively, these conditions, which cluster in diabetic individuals, can lead to damaged or impaired vascular endothelial cell function and accelerated vascular disease. Thus, treatments that both promote blood glucose tolerance and reduce a diabetic's risk for vascular diseases are desirable.

Such treatments may include diets that attempt to control and optimize the intake of certain dietary components such as fatty acids. Fatty acids are carboxylic acids and are classified based on the length and saturation characteristics of the carbon chain. Short chain fatty acids have 2 to about 4 carbons and are typically saturated. Medium chain fatty acids have from about 6 to about 10 carbons and are also typically saturated. Long chain fatty acids have from about 12 to about 24 or more carbons and may also be saturated or unsaturated. In longer fatty acids there may be one or more double bonds (unsaturation), giving rise to the terms "monounsaturated" and "polyunsaturated", respectively.

Longer chain lipids are categorized according to the number and position of double bonds in the fatty acids according to a nomenclature well understood by the biochemist. Biochemists often group long chain polyunsaturated fatty acids (LCPUFA) into series or families based on the position of the double bond in the carbon chain. The family to which an LCPUFA belongs is determined by the position of the double bond closest to the methyl end of the fatty acid. For example, the omega-3 series (or n-3 series) contains a first double bond at the third carbon from the methyl end of the fatty acid, the omega-6 series (or n-6 series) contains its first double bond at the sixth carbon, and the omega-9 series (or n-9 series) has no double bond until the ninth carbon. Alpha-linolenic acid, for example, has a chain length of 18 carbons and has 3 double bonds with the first double bond from the methyl end located at the third carbon making it a member of the omega-3 family. A short hand nomenclature has been developed to provide all this information about a fatty acid at a glance. The nomenclature is: [chain length]:[number of double bonds]n-[position of the double bond closest to the methyl end of the fatty acid]. Thus, alpha-linolenic acid (ALA) is referred to as "C18:3n-3". Similarly, docosahexanoic acid (DHA) has a chain length of 22 carbons with 6 double bonds beginning with the third carbon from the methyl end and, thus, is designated "C22:6n-3". Another LCPUFA is eicosapentaenoic acid (EPA) which is designated "C20:5n-3".

Diets rich in omega-3 fatty acids have been associated with a low incidence of type 2 diabetes. Studies have mostly focused on the omega-3 fatty acids EPA (C20:5n-3) and DHA (C22:6n-3), which are found in marine oils. ALA (C18:3n-3) is another omega-3 fatty acid that has not been studied as intensely as eicosapentaenoic acid (EPA) and docosahexanoic acid (DHA). Alpha-linolenic acid (ALA) can be metabolized in the body to eicosapentaenoic acid and docosahexanoic acid by the multiple enzymatic steps involving enzymes such as desaturase and elongase. Investigations that have been made into the benefit of alpha-linolenic acid with animal models on diabetics have reported mixed results. For example, two studies have evaluated the effects of alpha-linolenic acid on glucose metabolism in a genetically insulin-resistant animal model. Kato et al., *Journal of Health Science* 46, 489-492 (2000), found a significant improvement in blood glucose response to insulin in genetically insulin-resistant diabetic mice (KK-Ay) 21 days after daily administration of alpha-linolenic acid by gavage. Hun et al., *Biochemical and Biophysical Research Communications* 259, 85-90 (1999), fed high fat diets containing perilla oil, which is rich in alpha-linolenic acid, to genetically insulin resistant diabetic mice (KK-Ay). Hun et al. found, in contrast to Kato et al., that blood glucose levels were not significantly different after 8 weeks compared to mice consuming diets with soybean oil, which is rich in omega-6 polyunsaturated fatty acids, or lard, which contains only saturated and monounsaturated fatty acids.

Other studies have evaluated the effect of linseed (flaxseed) oil capsules on glucose metabolism in humans with type 2 diabetes mellitus or insulin resistance. McManus et al., *Diabetes Care* 19, 463-467 (1996), reported no difference in fasting glucose or insulin levels, or insulin sensitivity after three months for individuals with type 2 diabetes mellitus who had consumed capsules containing either linseed oil or fish oil. Goh et al., *Diabetologia* 40, 45-52 (1997), reported no differences in fasting glucose or insulin levels after three months when individuals with type 2 diabetes mellitus consumed oil capsules containing linseed oil or fish oil. In contrast, Nestel et al., *Arteriosclerosis, Thrombosis, and Vascular Biology* 17, 1163-1170 (1996), reported that insulin sensitivity decreased when obese individuals with markers of insulin resistance consumed diets rich in alpha-linolenic acid provided as margarine and muffins made with flaxseed oil.

Several patents disclose the use of lipid profiles containing omega-3, omega-6 and omega-9 fatty acids. For example, U.S. Pat. No. 5,780,451 (the "'451 patent") to DeMichele et al. discloses a nutritional product for persons with ulcerative colitis that utilizes omega-3, omega-6 and omega-9 fatty acids within specified percentage ranges. The ratio of omega-6 to omega-3 fatty acids of the '451 patent is disclosed as being in the range of 0.25:1 to 4.0:1 (ratios based on weight). Of the several omega-3 fatty acids used in the '451 patent, eicosapentaenoic acid is the most prevalent (with a preferred range based on weight of 16.0% to 19.6%) and alpha-linolenic acid is the least prevalent (with a preferred range based on weight of 1.5% to 2.1%). The specified ratio of linoleic acid to alpha-linolenic acid is in the range of 3.0 to 10.0 (ratios based on weight).

U.S. Pat. No. 4,921,877 to Cashmere et al. discloses a liquid nutritional product for use by glucose intolerant persons. Table 1 of the '877 patent discloses the preferred ingredients which include soy oil, high oleic safflower oil, and soy lecithin. These components create a lipid system containing an omega-9 fatty acid (oleic acid), an omega-6 fatty acid (linoleic acid), and an omega-3 fatty acid (alpha-linolenic acid). The omega-3 component of this system is only present at a relatively low percentage by weight (approximately 1.2% of the lipid system).

Other patents specify an optimal ratio for omega-6 to omega-3 fatty acids, but do not disclose an optimal ratio for omega-9 to omega-3 fatty acids. For example, U.S. Pat. No. 5,308,832 to Garleb et al. discloses a nutritional product for use by persons with a neurological injury. The '832 patent discloses a multi-component lipid blend (see Table 8 of the '832 patent) and specifies a ratio of omega-6 to omega-3 fatty acids in the range by % weight of 1 to 6. No preferred ratio of omega-9 to omega-3 fatty acids is disclosed. Also, U.S. Pat. No. 5,922,704 (the "'704 patent") to Bland discloses nutritional supplements for men. The '704 patent discloses the use of linoleic acid (omega-6) and alpha-linolenic acid (omega-3) in a ratio of 1:2. No preferred ratio of omega-9 to omega-3 fatty acids is disclosed.

SUMMARY OF THE INVENTION

One embodiment of the invention provides a lipid system. Long chain polyunsaturated fatty acids (LCPUFAs) from each of the omega-3, omega-6, and omega-9 families are included in the lipid system. A range of ratios based on weight % for omega-6 to omega-3 LCPUFAs of about 0.25:1 to about 3:1. A range of ratios based on weight % for omega-9 to omega-3 LCPUFAs of about 0.4:1 to about 3:1. Saturated fatty acids with more than 12 carbon atoms may optionally be further added to the lipid system at levels of less than about 47 g/100 g total lipid. Preferably, several oils can be combined to achieve the omega-6 to omega-3 and omega-9 to omega-3 fatty acid ratios specified above.

The lipid system of the present embodiment provides optimized ratios of essential and non-essential fatty acids that can improve the glucose tolerance of a glucose intolerant individual, improve the insulin sensitivity of an insulin resistant individual, and reduce the risk of vascular disease in a individual at risk for vascular disease. The lipid system may be administered to glucose intolerant individual, insulin resistant individual, and individual at risk for vascular disease. The lipid system may also be administered to individual other than those that are glucose intolerant, insulin resistant, or at risk for vascular disease.

The lipid system of the invention may be administered to an individual in any orally acceptable dosage form, and combinations thereof. Nutritional formulas include enteral formulas, oral formulas, formulas for adults, formulas for pediatric individuals and formulas for infants. Nutritional formulas contain a protein component, providing from about 5 to about 35% of the total caloric content of the formula, a carbohydrate component providing from about 10 to about 95% of the total caloric content, and a lipid component providing from about 5 to about 70% of the total caloric content. The nutritional formulas described herein may be used as a supplement to the diet or sole source of nutrition.

Another embodiment of the invention provides a method for improving the glucose tolerance of a glucose intolerant individual. The method of the present embodiment comprises administering a lipid system as described herein.

Another embodiment of the invention provides a method for improving the insulin sensitivity of an insulin resistant individual. The method of the present embodiment comprises administering a lipid system as described herein.

Another embodiment of the invention provides a method for reducing the risk of vascular disease in an individual at risk for vascular disease. The method of the present embodiment comprises administering a lipid system as described herein.

DETAILED DESCRIPTION

Figure 1:
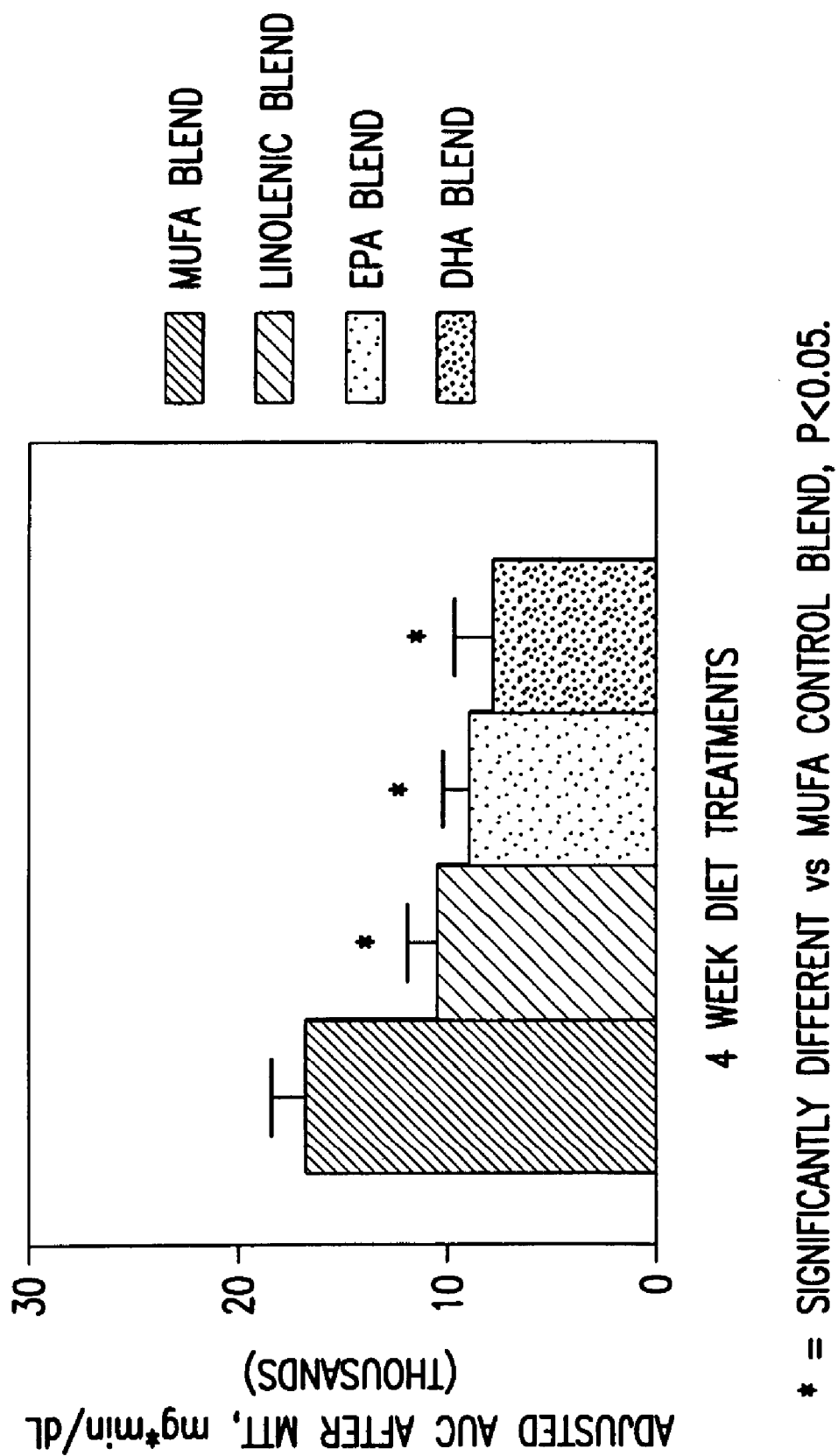
FIG. 1 is an area under the curve bar graph of the Meal Tolerance Test blood glucose results after 4 weeks of diet treatment after the data was adjusted to baseline. Group 1 Control MUFA blend; Group 2 Linolenic blend; Group 3 EPA blend; and Group 4 DHA blend.

As used herein, the term "lipid" generally denotes a heterogeneous group of substances associated with living systems which have the common property of being insoluble in water, can be extracted from cells by organic solvents of low polarity such as chloroform and ether.

The term "structured glyceride" or "structured lipid" refers to an oil or fat that contains specific fatty acyl residues in a specific position on the glycerol backbone. A glyceride is an ester of glycerol (1,2,3-propanetriol) with acyl radicals of fatty acids and is also known as an acylglycerol. If only one position of the glycerol molecule is esterified with a fatty acid, a "monoglyceride" is produced; if two positions are esterified, a "diglyceride" is produced; and if all three positions of the glycerol are esterified with fatty acid a "triglyceride" or "triacylglycerol" is produced. A glyceride is called "simple" if all esterified positions contain the same fatty acid; or "mixed" if different fatty acids are involved. The carbons of the glycerol backbone are designated sn-1, sn-2 and sn-3, with sn-2 being in the middle and sn-1 and sn-3 being sterically equivalent for esterification purposes. Naturally occurring oils and fats consist largely of triglycerides wherein the 3 fatty acyl residues may or may not be identical, i.e. both simple and mixed triglycerides. The term "long chain triglycerides (LCT)" means a triglyceride containing fatty acids with more than 12 carbon atoms (long chain fatty acids—"LCFA"), whereas the term "medium chain triglycerides (MCT)" means a triglyceride containing fatty acids with 6 to 10 carbon atoms.

A "high MUFA, low saturated fatty acid diet" refers to a diet in which less than 10% of the fat intake is saturated fatty acids, while the MUFAs are the predominant fatty acids.

A lipid system is disclosed herein. This lipid system is suitable for independent use or as a component of a nutritional product. The level of a particular fatty acid in a composition may be expressed in relative amounts or ratios. Herein, the ratios between long chain poly-unsaturated fatty acid (LCPUFA) families are often discussed. For example, if the omega-6 fatty acids in a lipid composition are present at a 60 weight % level and the omega-3 fatty acids in the same composition are present at a 30 weight % level, the omega-6 to omega-3 ratio is 2:1 regardless of the total fatty acid level or the weight or the volume of the individual acids. Describing the relationships between LCPUFA families in this manner is useful because the ratio is dimensionless and, thus, comparative numbers are easily obtained.

One embodiment of the invention provides a lipid system. LCPUFAs from each of the omega-3, omega-6, and omega-9 families are included in the lipid system. A range of ratios based on weight % for omega-6 to omega-3 LCPUFAs of about 0.25:1 to about 3:1, preferably about 0.3:1 to about 2.5:1, and more preferably about 0.73:1 is provided. A range of ratios based on weight % for omega-9 to omega-3 LCPUFAs of about 0.4:1 to about 3:1, preferably about 1:1 to about 3:1, and more preferably about 2:1 is provided.

Saturated fatty acids with more than 12 carbon atoms may optionally be further added to the lipid system at levels of less than about 47 g/100 g total lipid, preferably less than about 20 g/100 g total lipid, and more preferably about 10 g/100 g total lipid are provided.

Examples of omega-3 fatty acids suitable for use by this lipid system include, but are not limited to, alpha-linolenic acid (C18:3n-3), stearidonic acid (C18:4n-3), eicosapentaenoic acid (C20:5n-3), docosapentaenoic acid (C22:5n-3), docosahexaenoic acid (C22:6n-3), and combinations thereof. Alpha-linolenic acid is an example of a preferred omega-3 fatty acid.

Examples of omega-6 fatty acids suitable for use by this lipid system include, but are not limited to, linoleic acid (C18:2n-6), gamma-linolenic acid (C18:3n-6), eicosadienoic acid (C20:2n-6), arachidonic acid (C20:4n-6), di-homo-gamma-linolenic acid (C20:3n-6), and combinations thereof. Linoleic acid is an example of a preferred omega-6 fatty acid.

Examples of omega-9 fatty acids suitable for use by this lipids system include, but are not limited to, oleic acid (C18:1n-9), elaidic acid (C18:1n-9), eicosenoic acid (C20:1n-9), erucic acid (C22:1n-9), nervonic acid (C24:1n-9), and combinations thereof. One knowledgeable in the art would understand that elaidic acid (C18:1n-9), erucic acid (C22:1n-9) are less preferred over concerns of toxicity. Oleic acid is an example of a preferred omega-9 fatty acid.

An example of a typical lipid system comprising 17-54% alpha-linolenic acid, 17-21% linoleic acid, 19-52% oleic acid, and less than 47% saturated fatty acids may satisfy these requirements.

These fatty acids are often present in naturally occurring oils. Examples of oils useful for this invention include, but not limited to, flaxseed oil, high oleic safflower oil, corn oil, and soy lecithin. Flaxseed oil (available from Bioriginal Food & Science Corp., Saskatoon, Saskatchewan, Canada ("Bioriginal"); Arista Indus., Wilton, Conn. ("Arista")) contains between about 15-20% oleic acid (omega-9), between about 12-17% linoleic acid (omega-6), and between about 50-65% alpha-linolenic acid (omega-3). High oleic safflower oil (available from California Oils Corp., Richmond, Calif. ("California Oils"); Arista) contains between about 75-80% oleic acid (omega-9) and between about 12-17% linoleic acid (omega-6). Corn oil (available from Arista) contains between about 55-60% linoleic acid (omega-6) and between about 25-30% oleic acid (omega-9). Soy lecithin (available from Central Soya, Fort Wayne, Ind.) contains between about 7-9% alpha-linolenic acid (omega-3), between about 55-60% linoleic acid (omega-6), and between about 12-15% oleic acid (omega-9). Because naturally occurring oils vary in fatty acid content, the amount of a particular batch of oil used according to the invention may vary depending on the fatty acid content of that batch.

Other examples of naturally occurring oils that contain one or more omega-3, omega-6, or omega-9 fatty acids include, but are not limited to, olive oil (Arista), canola oil (CanAmera Foods, Inc., Oakville, Ontario; Arista), cottonseed oil (Arista), peanut oil (Arista), rice bran oil (Arista), rapeseed oil (CYB Group PLC, Kent, England), soybean oil (Arista), evening primrose oil (Bioriginal), borage oil (Bioriginal; Arista), safflower oil (California Oils), sunflower oil (Arista), high oleic sunflower oil (Arista), tuna oil (Arista), and sardine oil (Arista). Other naturally occurring oils that are not commonly commercially available, such as, perilla oil, may also be used with the invention.

Other potentially useful naturally occurring oils that provide saturated fatty acids while providing relatively insignificant amounts of omega-3, omega-6, or omega-9 fatty acids include, but are not limited to, coconut oil (Arista), palm kernel oil (USA Chemicals Inc., Arkansas ("USChemicals")), palm oil (Arista), cocoa butter oil (USChemicals), and other medium chain triglyceride oils. Commercial sources for naturally occurring oils are readily available and known to one practicing in the art and should not be construed as limited to those listed herein. These naturally occurring oils may be obtained from the sources indicated above. The scope of this invention is not intended to be limited by this list of known naturally occurring oils or even oils known for use in nutritional products, but is meant to encompass the use of any oil that may be discovered in the future. Additionally, the scope of the invention is intended to include the use of novel (e.g., single-celled, plant, mammalian, or fractions (e.g. ethyl esters)), transgenic, synthetic, or purified oils now known or developed in the future that contain the specific ratios listed above.

In addition to these food grade oils, the LCPUFAs of the invention may be incorporated into structured lipids, which may be incorporated into nutritional formulas and/or supplements if desired. Structured lipids are known in the art. A concise description of structured lipids can be found in INFORM, Vol. 8, no. 10, page 1004, entitled Structured lipids allow fat tailoring (October 1997). Also see U.S. Pat. No. 4,871,768, which is hereby incorporated by reference. Structured lipids are predominantly triacylglycerols containing mixtures of medium and long chain fatty acids on the same glycerol backbone. Structured lipids and their use in enteral formula are also described in U.S. Pat. Nos. 6,194,379 and 6,160,007, the contents of which are hereby incorporated by reference.

Preferably, several oils are combined to achieve the omega-6 to omega-3 and omega-9 to omega-3 fatty acid ratios specified above. An example of a lipid system that meets the requirements of this invention is a combination of flaxseed oil, high oleic safflower oil and corn oil in the proportions listed in Table 1.

TABLE 1

Example Lipid System Composition

| Oil | wt. % |
| --- | --- |
| Flaxseed | 41 |
| High Oleic Safflower | 53 |
| Corn | 6 |

Lipid systems comprising 30-90% flaxseed oil, 0-60% high oleic safflower oil and 0-10% corn oil may satisfy the requirements specified above. Optionally, soy lecithin may be added from 0-7% of the fat system to act as an emulsifier. The combination of the naturally occurring oils listed in Table 1 provides the fatty acid profile listed in Table 2 (as determined by gas chromatography using a HP Model 5890 series II plus gas chromatograph (Hewlett-Packard, Avondale, Pa.) with an Omegawax 320 fused silica capillary column (0.32 mm×30 m×0.25 μm; Supelco, Bellefonte, Pa.)).

TABLE 2

Fatty Acid Profile of Lipid System Listed in Table 1.

| Fatty Acid | wt. % |
| --- | --- |
| Oleic (C18: 1n-9) | 49.52 |
| Linoleic (C18: 2n-6) | 17.99 |
| Alpha-Linolenic (C18: 3n-3) | 24.6 |
| Saturated Fatty Acids | 6.7 |
| Other | 0.4 |

Because the fatty acid composition of individual naturally occurring oils varies by batch, the exact weight percentages of omega-3, omega-6, and omega-9 fatty acids in a combination of oils will also vary. In the example lipid system described in Table 1 and Table 2, the ratio of omega-6 to omega-3 fatty acids, i.e., linoleic acid to alpha-linolenic acid, is about 0.7:1. And the ratio of omega-9 to omega-3 fatty acids, i.e., oleic acid to alpha-linolenic acid, is about 2.0:1. This lipid system meets the requirements described above and was used in the study described below (see Group 2 lipid system).

The lipid system of the present embodiment provides optimized ratios of essential and non-essential fatty acids that can improve the glucose tolerance of a glucose intolerant individual, improve the insulin sensitivity of an insulin resistant individual, and reduce the risk of vascular disease in a individual at risk for vascular disease. The lipid system may be administered to glucose intolerant individual, insulin resistant individual, and individual at risk for vascular disease. The lipid system may also be administered to individual other than those that are glucose intolerant, insulin resistant, or at risk for vascular disease. Preferably, the individual administered the lipid system of the present invention are human, but the scope of the invention is not limited to humans.

Glucose intolerant individuals have an exaggerated blood glucose response to dietary carbohydrates, e.g., glucose. Administering the lipid system described above to a glucose intolerant individual may minimize postprandial glucose response. Improving the glucose tolerance means reducing the exaggerated blood glucose response of a glucose intolerant individual. Whether an individual has an exaggerated blood glucose response to dietary carbohydrate can be determined by assessing blood glucose levels up to two hours after the individual has consumed a controlled level of glucose (oral glucose tolerance test) or other carbohydrate source or meal. Improvement in the glucose tolerance of a glucose intolerant individual may be determined by standard glucose tolerance testing or by any other testing known to one of skill in the art.

Improving the insulin sensitivity of an insulin resistant individual means increasing insulin-mediated glucose disposal, i.e., minimizing resistance to insulin. Administering the lipid system described above to an insulin resistant individual may enhance postprandial insulin sensitivity. Insulin sensitivity can be assessed by measuring how blood insulin fluctuates during a glucose tolerance test (i.e., if less insulin is secreted to control blood glucose, an improvement in insulin tolerance will be indicated) or by delivering insulin to an individual then monitoring blood glucose level (i.e., if glucose levels drop after insulin delivery sensitivity will be indicated). Improvement in the insulin sensitivity of an insulin resistant individual may be determined by standard insulin tolerance testing or by any other testing method known to one of skill in the art.

Combining glucose control with improved insulin sensitivity and a proper diet helps to reduce the risk of vascular disease in individuals at risk for vascular disease. Therefore, administering the lipid system described above to an individual at risk for vascular disease may reduce the risk of vascular disease. Reducing the risk of vascular disease in an individual at risk for vascular disease means improving the ability of the arteries of an individual's circulatory system to vasodilate, i.e., expand in response to increased blood flow needs. Various risks for vascular disease may include, but are not limited to, impaired vascular function or elevated blood lipid levels. Types of vascular function that may be impaired include, but are not limited to, vasodilation, blood flow (reduced), and blood pressure (high). And the types of blood lipids that may be elevated include, but are not limited to, triglycerides and free fatty acids. Reduction in the risk of vascular disease may be indicated by improved vascular function, i.e., improved vasodilation, increased blood flow, and reduced blood pressure, or reduced levels of blood lipids, i.e., triglycerides and free fatty acids. Methods for testing an individual to determine if their risk of vascular disease has decreased are well know to those of skill in the art (ie., measuring blood pressure, pulse pressure in extremities, arterial diameter via ultrasound).

The lipid system of the invention may be administered to an individual in the form of a dietary supplement or as a nutritional product.

The lipid system of the present embodiment may be administered in any orally acceptable dosage form, and combinations thereof. Examples of such dosage forms include, for example, chewable tablets, quick dissolve tablets, effervescent tablets, reconstitutable powders, elixirs, liquids, solutions, suspensions, emulsions, tablets, multi-layer tablets, bi-layer tablets, capsules, soft gelatin capsules, hard gelatin capsules, caplets, lozenges, chewable lozenges, beads, powders, granules, particles, microparticles, dispersible granules, cachets, and combinations thereof. The preparation of the above dosage forms are well known to persons of ordinary skill in the art.

Typically a "vehicle or carrier" may be used to incorporate the lipid system. In addition to the pharmaceutical dosage forms listed above, nutritious "vehicles or carriers" include, but are not limited to, the FDA statutory food categories: conventional foods, foods for special dietary uses, dietary supplements and medical foods. Generally speaking, nutritional products contain macronutrients, such as, lipids, proteins, and carbohydrates, in varying relative amounts depending on the age and condition of the intended user. Nutritional products often also contain micronutrients such as vitamins, minerals and trace minerals. "Foods for special dietary uses" are intended to supply a special dietary need that exists by reason of a physical, physiological, pathological condition by supplying nutrients to supplement the diet or as the sole item of the diet. A "dietary supplement" is a product intended to supplement the diet by ingestion in tablet, capsule or liquid form and is not represented for use as a conventional food or as a sole item of a meal or the diet. A "medical food" is a food which is formulated to be consumed or administered enterally under the supervision of a physician and which is intended for the specific dietary management of a disease or condition for which distinctive nutritional requirements, based on recognized scientific principles, are established by medical evaluation. These nutritional products can be manufactured by generally conventional techniques known to those skilled in the art.

The lipid system of the instant invention may be delivered to an individual in the form of a concentrated liquid for example. Syrups, honeys and elixirs may be admixed with the lipid system to improve the flavor. Oil in water emulsions may be better suitable for oral use because these are water-miscible and thus their oiliness is masked. Emulsions are well known in the pharmaceutical sciences. The lipid system of this invention can be manufactured using techniques well known to those skilled in the art. Generally speaking, an emulsifying agent is dissolved in the oil. The emulsifier/oil mixture may be added directly to the water to form an oil in water emulsion. Alternatively, the emulsifying agent is dissolved in the water and the oil is added, with agitation, to the emulsifier/aqueous solution. Examples, of typical natural emulsifying agents include gelatin, egg yolk, casein, wool fat, cholesterol, acacia, tragacanth, chondrus and pectin. The mixtures require physical manipulation to achieve the emulsified physical state. Emulsification equipment includes a wide variety of agitators, homogenizers, colloid mills and ultrasonic devices. An emulsion of the lipid system of the instant invention may be stored in conventional containers and may be dispensed in small but precise quantities or unit dosages. Such dosages are characteristically dispensed using a pipette and compressible, resilient bulb dropper assembly or graduated measuring containers.

The composition of the present inventive subject matter may be administered in a partial, fractional dose, one or more times during a 24 hour period; a single dose during a 24 hour period of time; a double dose during a 24 hour period of time; or more than a double dose during a 24 hour period of time. Fractional, double or other multiple doses may be taken simultaneously or at different times during the 24 hour period. The target dose is at least about 1 gm of n-3 fatty acids described above per day in a high MUFA, low saturated fatty acid diet, preferable at least about 3 gm of n-3 fatty acids described above per day in a high MUFA, low saturated fatty acid diet.

Alternatively, the lipid system of the instant invention may be delivered in soft gelatin capsules, more commonly known as soft gels. Soft gels are widely used in the pharmaceutical industry as an oral dosage form containing many different types of pharmaceutical and vitamin products. Soft gels are available in a great variety of sizes and shapes, including round shapes, oval shapes, oblong shapes, tube shapes and other special types of shapes such as stars. The finished capsules or soft gels can be made in a variety of colors. Also, opacifiers may be added to the shell. Soft gels are predominantly employed for enclosing liquids, more particularly oily solutions, suspensions or emulsions. Filling materials normally used are vegetable, animal or mineral oils, liquid hydrocarbons, volatile oils and polyethylene glycols.

The soft gelatin capsules containing the lipid system of this invention can be manufactured using techniques well known to those skilled in the art. U.S. Pat. Nos. 4,935,243, 4,817,367 and 4,744,988 are directed to the manufacturing of soft gelatin capsules. Manufacturing variations are certainly well known to those skilled in the pharmaceutical sciences. Typically, soft gels comprise an outer shell primarily made of gelatin, a plasticizer, and water, and a fill contained within the shell. The fill may be selected from any of a wide variety of substances that are compatible with the gelatin shell.

Generally speaking, a gelatin capsule manufacturing system is comprised of three main systems: a sheet forming unit, a capsule forming unit, and a capsule recovery unit. A gelatin hopper supplies the gelatin to the tank where a heater melts the gelatin. The melted gelatin is delivered to the spreading box where the desired size, shape and thickness of the gelatin sheet is formed and discharged out of the spreader box to a cooling drum. The cooling drum cools the gelatin sheet as the gelatin sheet is transported to the capsule-forming unit. A pair of cooled gelatin sheets is inserted between a pair of die rolls fitted with the desired die heads in the capsule-forming unit. At the same time, the fill liquid nozzle is positioned so as to discharge the desired amount of fill liquid between two gelatin sheets. The discharging timing is adjusted so that the recess formed by the die heads are filed with fill liquid as the gelatin sheets are brought into contact with each other, which allows filled capsules to be formed. Die roll scraping brushes remove the formed gelatin capsules from the die heads. The gelatin capsules are subsequently collected into a bulk container for storage prior to filing into the desired container. The resultant gelatin capsules are then packaged according to market need, i.e., unit dose, rolls, bulk bottles, blister packs, etc.

Soft gels present a number of advantages over other forms of oral administration. They are, for instance, odorless and tasteless, easy to swallow, and their swelling properties and solubility in water ensure that the active substances are easily released in the stomach. The soft gel capsule is the preferred method of delivery for the instant invention due to LCPUFA sensitivity to oxidation and light.

Typically, the unit dosage is one soft gel capsule comprising at least 1 gm of fatty acids in the ratios of the instant invention. Typically, at least 1 soft gel cap is administered per day, preferably at least 3 soft gel caps are administered per day.

Optionally, additional nutrients relevant to the type 2 diabetic may be added to the lipid system emulsions and soft gel caps dosage forms. The practitioner understands that certain micronutrients may have potential benefit for people with diabetes such as the antioxidants vitamin E, beta-carotene, vitamin C, selenium, BHA and BHT.

Another embodiment of the invention provides a nutritional product. The nutritional product of this embodiment comprises the lipid system as described above in combination with a macronutrient. Macronutrients include proteins, carbohydrates, and mixtures thereof. Micronutrients such as vitamins, minerals and trace minerals may also be included in the nutritional product. The nutritional product of the present embodiment provides optimized ratios of essential fatty acids that can improve the glucose tolerance of a glucose intolerant individual, improve the insulin sensitivity of an insulin resistant individual, and reduce the risk of vascular disease in an individual at risk for vascular disease. The nutritional product may be administered to glucose intolerant individuals, insulin resistant individuals, and individuals at risk for vascular disease. The nutritional product may be administered to individuals other than glucose intolerant individuals, insulin resistant individuals, and individuals at risk for vascular disease. Preferably, the individuals administered the nutritional product of the present invention are human, but the scope of the invention is not limited to humans.

Nutritional formulas include enteral formulas, oral formulas, formulas for adults, formulas for pediatric individuals and formulas for infants. Nutritional formulas contain a protein component, providing from about 5 to about 35% of the total caloric content of the formula, a carbohydrate component providing from about 10 to about 95% of the total caloric content, and a lipid component providing from about 5 to about 70% of the total caloric content. The nutritional formulas described herein may be used as a supplement to the diet or sole source of nutrition. The amount of calories and nutrients required will vary from person to person, dependent upon such variables as age, weight, and physiologic condition. The amount of nutritional formula needed to supply the appropriate amount of calories and nutrients may be determined by one of ordinary skill in the art, as may the appropriate amount of calorie and nutrients to incorporate into such formulas.

As examples, when the formula is designed for the adult population, the protein component may comprise from about 9 to about 30% of the total caloric content of said nutritional formula; the carbohydrate component may comprise from about 15 to about 90% of the total caloric content of said nutritional formula; and the lipid component may comprise from about 5 to about 50% of the total caloric content of said nutritional formula. The adult nutritional formula may typically be in liquid, semi-solid, solid or powder form.

As another example, when the formula is designed for a non-adult population, the protein component may comprise from about 8 to about 25% of the total caloric content of said nutritional formula; the carbohydrate component may comprise from about 35 to about 50% of the total caloric content of said nutritional formula; and the lipid component may comprise from about 30 to about 60% of the total caloric content of said nutritional formula. These ranges are provided as examples only, and are not intended to be limiting.

Any food grade oils, structured lipids, fatty acids and combinations thereof may be added to the nutritional formula to obtain the LCPUFA ratios of the instant invention. Typically, the fat system of the nutritional comprises 30-90% flaxseed oil, 0-59% high oleic safflower oil and 0-7% corn oil.

The proteins that may be utilized in the nutritional products of the invention include any proteins suitable for human consumption. Such proteins are well known by those skilled in the art and can be readily selected when preparing such products. Examples of suitable proteins that may be utilized typically include casein, whey, milk protein, soy, pea, rice, corn, hydrolyzed protein and mixtures thereof. Protein can be provided in different forms including intact, hydrolyzed, and as free amino acids. A protein source may be supplemented with various free amino acids in order to provide a more nutritionally complete and balanced amino acid profile. Examples of suitable free amino acids include, but are not limited to, tryptophan, tyrosine, cystine, taurine, L-methionine, L-arginine, and carnitine. As indicated above, the typical amount of protein in the nutritional product is from about 5% to about 35% of total calories, more preferably from about 15% to about 25% of total calories.

Commercial protein sources are readily available and known to one practicing in the art. For example, caseinates, whey, hydrolyzed caseinates, hydrolyzed whey and milk proteins are available from New Zealand Milk Products of Santa Rosa, Calif. Soy and hydrolyzed soy proteins are available from Protein Technologies International of St. Louis, Mo. Pea protein is available from Feinkost Ingredients Company of Lodi, Ohio. Rice protein is available from California Natural Products of Lathrop, Calif. Corn protein is available from EnerGenetics Inc. of Keokuk, Iowa.

Examples of carbohydrate sources for nutritional products include hydrolyzed or intact, naturally and/or chemically modified starches obtained from corn, tapioca, rice or potato, in waxy or non-waxy forms. Other examples of carbohydrates include hydrolyzed cornstarch, maltodextrin, glucose polymers, sucrose, maltose, lactose, corn syrup, corn syrup solids, glucose, fructose, high fructose corn syrup and indigestible oligosaccharides, such as fructooligosaccharides (FOS). Any single carbohydrate listed above, or any combination thereof, as appropriate may be utilized. Other suitable carbohydrates will be readily apparent to those skilled in the art. As indicated above, the typical amount of carbohydrate in the nutritional product is from about 10% to about 95% of total calories, more preferably from about 15% to about 90% of total calories.

Commercial sources for the carbohydrates listed above are readily available and known to one practicing the art. For example, corn syrup solids are available from Cerestar USA, Inc in Hammond, Ind. Glucose and rice based syrups are available from California Natural Products in Lathrop, Calif. Various corn syrups and high fructose corn syrups are available from Cargil in Minneapolis, Minn. Fructose is available from A.E. Staley in Decatur, Ill. Maltodextrin, glucose polymers, hydrolyzed corn starch are available from American Maize Products in Hammond, Ind. Sucrose is available from Domino Sugar Corp. in New York, N.Y. Lactose is available from Foremost in Baraboo, Wis. and indigestible oligosaccharides, such as FOS, are available from Golden Technologies Company of Golden, Colo.

The nutritional compositions of the invention typically contain vitamins and minerals. Vitamins and minerals are understood to be essential in the daily diet. Those skilled in the art appreciate that minimum requirements have been established for certain vitamins and minerals that are known to be necessary for normal physiological function. Practitioners also understand that appropriate additional amounts of vitamin and mineral ingredients need to be provided to nutritional compositions to compensate for some loss during processing and storage of such compositions. Additionally, the practitioner understands that certain micronutrients may have potential benefit for people with diabetes such as chromium, carnitine, taurine and vitamin E and that higher dietary requirements may exist for certain micro nutrients such as ascorbic acid due to higher turnover in people with type 2 diabetes.

An example of the vitamin and mineral system for a complete nutritional product used as a sole source of nutrition typically comprises at least 100% of the RDI for the vitamins A, $B_1$, $B_2$, $B_6$, $B_{12}$, C, D, E, K, beta-carotene, Biotin, Folic Acid, Pantothenic Acid, Niacin, and Choline; the minerals calcium, magnesium, potassium, sodium, phosphorous, and chloride; the trace minerals iron, zinc, manganese, copper, and iodine; the ultra trace minerals chromium, molybdenum, selenium; and the conditionally essential nutrients m-inositol, carnitine and taurine in from about 350 Kcal to about 5600 Kcal.

An example of the vitamin and mineral system for a nutritional product used as a nutritional supplement typically comprises at least 25% of the RDI for the vitamins A, $B_1$, $B_2$, $B_6$, $B_{12}$, C, D, E, K, beta-carotene, Biotin, Folic Acid, Pantothenic Acid, Niacin, and Choline; the minerals calcium, magnesium, potassium, sodium, phosphorous, and chloride; the trace minerals iron, zinc, manganese, copper, and iodine; the ultra trace minerals chromium, molybdenum, selenium; and the conditionally essential nutrients m-inositol, carnitine and taurine in a single serving or from about 50 Kcal to about 800 Kcal.

Artificial sweeteners may also be added to the nutritional product to enhance the organoleptic quality of the formula. Examples of suitable artificial sweeteners include saccharine, aspartame, acesulfame K and sucralose. The nutritional products of the present invention will also desirably include a flavoring and/or color to provide the nutritional products with an appealing appearance and an acceptable taste for oral consumption. Examples of useful flavorings typically include, for example, strawberry, peach, butter pecan, chocolate, banana, raspberry, orange, blueberry and vanilla.

The nutritional products of this invention can be manufactured using techniques well known to those skilled in the art. For liquid nutritional, generally speaking, an oil and fiber blend is prepared containing all oils, any emulsifier, fiber and the fat soluble vitamins. Three more slurries (carbohydrate and two protein) are prepared separately by mixing the carbohydrate and minerals together and the protein in water. The slurries are then mixed together with the oil blend. The resulting mixture is homogenized, heat processed, standardized with water soluble vitamins, flavored and the liquid terminally sterilized or dried to produce a powder. Alternatively, the homogenized formula may be kept undiluted and filled into appropriate containers as pudding or dried to form powder. The product is then packaged. Typically the package will provide directions for use by the end consumer (i.e., to be consumed by a diabetic) Solid nutritional compositions such as bars, cookies, etc. may also be manufactured utilizing techniques known to those skilled in the art. For example, they may be manufactured using cold extrusion technology as is known in the art. To prepare such compositions, typically all of the powdered components will be dry blended together. Such constituents typically include the proteins, vitamin premixes, certain carbohydrates, etc. The fat soluble components are then blended together and mixed with the powdered premix above. Finally any liquid components are then mixed into the composition, forming a plastic like composition or dough.

The process above is intended to give a plastic mass which can then be shaped, without further physical or chemical changes occurring, by the procedure known as cold forming or extrusion. In this process, the plastic mass is forced at relatively low pressure through a die, which confers the desired shape. The resultant exudate is then cut off at an appropriate position to give products of the desired weight. If desired the solid product is then coated, to enhance palatability, and packaged for distribution. Typically the package will provide directions for use by the end consumer (i.e., to be consumed by a diabetic)

The solid nutritionals of the instant invention may also be manufactured through a baked application or heated extrusion to produce cereals, cookies, and crackers. One knowledgeable in the arts would be able to select one of the many manufacturing processes available to produce the desired final product.

Another embodiment of the invention provides a method for improving the glucose tolerance of a glucose intolerant individual. The method of the present embodiment comprises administering a lipid system as described above. As discussed above, administering the lipid system described above or a nutritional product or dietary supplement incorporating the lipid system described above can improve the glucose tolerance of a glucose intolerant individual.

Another embodiment of the invention provides a method for improving the insulin sensitivity of an insulin resistant individual. The method of the present embodiment comprises administering a lipid system as described above. As discussed above, administering the lipid system described above or a nutritional product or dietary supplement incorporating the lipid system described above can improve the insulin sensitivity of an insulin resistant individual.

Another embodiment of the invention provides a method for reducing the risk of vascular disease in an individual at risk for vascular disease. The method of the present embodiment comprises administering a lipid system as described above. As discussed above, administering the lipid system described above or a nutritional product or dietary supplement incorporating the lipid system described above can reduce the risk of vascular disease in an individual at risk for vascular disease.

Example A

Table 3 presents a bill of materials for manufacturing 1,000 kilograms of an unflavored liquid nutritional product according to the present invention. A detailed description of its manufacture follows.

TABLE 3

| Bill of Materials for Unflavored Liquid Nutritional | |
|---|---|
| Ingredient | Quantity per 1,000 Kg |
| Water | 840 Kg |
| Maltrin-100 | 56 Kg |
| Acid Casein | 41.093 Kg |
| Fructose | 28 Kg |
| High Oleic Safflower Oil | 17 Kg |
| Maltitol Syrup | 16 Kg |
| Flax oil | 13.26 Kg |
| Maltitol Powder | 12.632 Kg |
| Fibersol 2(E) | 8.421 Kg |
| Calcium caseinate | 6.043 Kg |
| Fructooligosaccharide | 4.607 Kg |
| Soy Polysaccharide | 4.3 Kg |
| micronized tricalcium phosphate | 2.8 Kg |
| magnesium chloride | 2.4 Kg |
| Corn oil | 2.04 Kg |
| soy lecithin | 1.7 Kg |
| sodium citrate | 1.18 Kg |
| potassium citrate | 1.146 Kg |
| sodium hydroxide | 1.134 Kg |
| magnesium phosphate | 1.028 Kg |
| m-inositol | |
| vitamin C | 584 gm |
| potassium chloride | 530 gm |
| choline chloride | 472.1 gm |
| 45% potassium hydroxide | 402.5 gm |
| utm/tm premix | 369.3 gm |
| potassium phosphate | 333 gm |
| carnitine | 230.5 gm |
| gellan gum | 125 gm |
| taurine | 100.1 gm |

TABLE 3-continued

Bill of Materials for Unflavored Liquid Nutritional

| Ingredient | Quantity per 1,000 Kg |
|---|---|
| vitamin E | 99 gm |
| WSV premix | 75.4 gm |
| Vitamin DEK premix | 65.34 gm |
| 30% beta carotene | 8.9 gm |
| vitamin A | 8.04 gm |
| pyridoxine hydrochloride | 3.7 gm |
| chromium chloride | 1.22 gm |
| folic acid | 0.64 gm |
| potassium iodide | 0.20 gm |
| cyanocobalamin | 0.013 gm |

WSV premix(per g premix): 375 mg/g niacinamide, 242 mg/g calcium pantothenate, 8.4 gm/g folic acid, 62 mg/g thiamine chloride hydrochloride, 48.4 gm/g riboflavin, 59.6 mg/g pyridoxine hydrochloride, 165 mcg/g cyanocobalamin and 7305 mcg/g biotin
Vitamin DEK premix(per g premix): 8130 IU/g vitamin $D_3$, 838 IU/g vitamin E, 1.42 mg/g vitamin $K_1$
UTM/TM premix(per g premix): 45.6 mg/g zinc, 54 mg/g iron, 15.7 manganese, 6.39 mg/g copper, 222 mcg/g selenium, 301 mcg/g chromium and 480 mcg/g molybdenium The liquid nutritional products of the present invention have been manufactured by preparing four slurries which are blended together, heat treated, standardized, packaged and sterilized. The process for manufacturing 1000 kilograms of a liquid nutritional product, using the bill of materials from Table 3 is described in detail below.

A carbohydrate/mineral slurry is prepared by first heating about 82 kilograms of water to a temperature of from about 65° C. to about 71° C. with agitation. With agitation, the required amount of sodium citrate and gellen gum distributed by the Kelco, Division of Merck and Company Incorporated, San Diego, Calif., U.S.A. under the product name "Kelcogel." is added and agitated for 5 minutes. The required amount of the ultra trace mineral/trace mineral (UTM/TM) premix (distributed by Fortitech, Schnectady, N.Y.) is added. The slurry is greenish yellow in color. Agitation is maintained until the minerals are completely dispersed. With agitation, the required amounts of the following minerals are then added: potassium citrate, potassium chloride, chromium chloride, magnesium chloride and potassium iodide. Next, the first maltodextrin distributed by Grain Processing Corporation, Muscataine, Iowa, U.S.A. under the product name "Maltrin M-100" and fructose are added to slurry under high agitation, and are allowed to dissolve. With agitation, the required amounts of maltitol powder distributed by Roquette America, Inc., Keokuk, Iowa under the product name Maltisorb Powder P35SK, maltitol syrup distributed by AlGroup Lonza, Fair Lawn, N.J. under the product name Hystar 5875, fructooligosaccharides distributed by Golden Technologies Company, Golden, Colo., U.S.A. under the product designation "Nutriflora-P Fructo-oligosaccharide Powder (96%)" and a second maltodextrin distributed by Matsutani Chemical Industry Co., Hyogo, Japan under the product name Fibersol 2(E) are added and agitated well until completely dissolved. The required amount of micronized tricalcium phosphate is added to the slurry under agitation. The completed carbohydrate/mineral slurry is held with agitation at a temperature from about 65° C. to about 71° C. for not longer than twelve hours until it is blended with the other slurries.

A fiber in oil slurry is prepared by combining and heating the required amounts of high oleic safflower oil and canola oil to a temperature from about 55° C. to about 65° C. with agitation. With agitation, the required amounts of the following ingredients are added to the heated oil: soy lecithin (distributed by Central Soya Company, Fort Wayne, Ind. under the product name Centrocap 162), Vitamin D, E, K premix (distributed by Vitamins Inc., Chicago, Ill.), vitamin A and beta-carotene. The required amounts of soy polysaccharide distributed by Protein Technology International, St. Louis, Mo. under the product name Fibrim 300 is slowly dispersed into the heated oil. The completed oil/fiber slurry is held under moderate agitation at a temperature from about 55° C. to about 65° C. for a period of no longer than twelve hours until it is blended with the other slurries.

A first protein in water slurry is prepared by heating 293 kilograms of water to 60° C. to 65° C. With agitation, the required amount of 20% potassium citrate solution is added and held for one minute. The required amount of acid casein is added under high agitation followed immediately by the required amount of 20% sodium hydroxide. The agitation is maintained at high until the casein is dissolved. The slurry is held from about 60° C. to 65° C. with moderate agitation.

A second protein in water slurry is prepared by first heating about 77 kilograms of water to a temperature of about 40° C. with agitation. The calcium caseinate is added and the slurry is agitated well until the caseinate is completely dispersed. With continued agitation, the slurry is slowly warmed to 60° C. to 65° C. The slurry is held for no longer than twelve hours until it is blended with the other slurries.

The batch is assembled by blending 344 kilograms of protein slurry one with 84 kilograms of protein slurry two. With agitation, the 37 kilograms of the oil/fiber slurry is added. After waiting for at least one minute, 216 kilograms of the carbohydrate/mineral slurry is added to the blended slurry from the preceding step with agitation and the resultant blended slurry is maintained at a temperature from about 55° C. to about 60° C. The pH of the blended batch is adjusted to a pH of 6.45 to 6.75 with 1N potassium hydroxide.

After waiting for a period of not less than one minute nor greater than two hours, the blend slurry is subjected to deaeration, ultra-high-temperature treatment, and homogenization, as follows: a positive pump is used to supply the blended slurry for this procedure; the blended slurry is heated to a temperature from about 71° C. to about 82° C.; the heated slurry is deareated at 10-15 inches Hg; the heated slurry is emulsified at 900 to 1100 psig in a single stage homogenizer; the emulsified slurry is passed through a plate/coil heater and preheated to from about 99° C. to about 110° C.; the preheated slurry is ultra high temperature heated by steam injection to a temperature of about 146° C. with a minimum hold time of about 5 seconds; the temperature of the UHT treated slurry is reduced to from about 99° C. to about 110° C. by passing it through a flash cooler; the temperature of the UHT treated slurry is reduced further to from about 71° C. to about 76° C. by passing it through a plate/coil heat exchanger; the UHT treated slurry is homogenized at 3900 to 4100/400 to 600 psig; the homogenized slurry is passed through a hold tube for at least 16 seconds at temperature from about 74° C. to about 80° C.; the homogenized slurry is cooled to a temperature from about 1° C. to about 7° C. by passing it through a heat exchanger; and the UHT treated and homogenized slurry is stored at a temperature from about 1° C. to about 7° C. with agitation.

After the above steps have been completed, appropriate analytical testing for quality control is conducted.

A water soluble vitamin (WSV) solution is prepared separately and added to the processed blended slurry.

The vitamin solution is prepared by adding the following ingredients to 9.4 kilograms of water with agitation: WSV premix (distributed by J.B. Laboratories, Holland, Mich.), vitamin C, choline chloride, L-carnitine, taurine, inositiol, folic acid, pyridoxine hydrochloride and cyanocobalamin. The required amount of 45% potassium hydroxide slurry is added to bring the pH to between 7 and 10.

Based on the analytical results of the quality control tests, an appropriate amount of water is added to the batch with agitation to achieve about 21% total solids. Additionally, 8.8 kilograms of vitamin solution is added to the diluted batch under agitation. The product pH may be adjusted to achieve optimal product stability. The completed product is then placed in suitable containers and subjected to terminal sterilization.

Example B

An alternative product form of the nutritional described in Example A is a semisolid or pudding. The product is manufactured as in Example A up through the heat treatment and homogenization step with the following addition. Two additional starches (distributed by A. E. Staley, Decatur, Ill. under the product names of Resista and Miraclear) are added to the carbohydrate slurry at 4.5 wt/wt % of total solids of the product. The water soluble vitamins and optional flavor are added to the undiluted blend. The pudding is filled at about 30 wt/wt % to 32 wt/wt % total solids into an appropriate container and terminally sterilized. Alternatively, the pudding is aseptically filled into appropriate containers.

Example C

Another product form of the nutritional described in Example A is a powder. The product is manufactured as in Example A up through the heat treatment and homogenization step. The water soluble vitamins and optional flavor are added to the undiluted blend. The blend is pumped to a tower dryer at about 45% to 55% total solids. Typical dryer parameters are as follows: nozzle pressure is 1400-2400 psig; liquid flow rate is 10 gpm max; ingoing air temperature is 211° C. max; outgoing air temperature is 87-104° C.; dryer chamber pressure is −0.2 to +0.2 inches of water.

To control bulk density, dispersibility, particle size, moisture and physical stability, the specific spray nozzle, nozzle pressure, drying temperatures and fine reinjection parameters may vary depending upon the drying conditions of the day. The powder passes from the dryer discharge cone into the powder cooler where it is cooled to about 43° C. The cooled powder is stored until it is filed into appropriate containers.

Example D

The nutritional of the instant invention may also be formulated as a nutritional bar. Although not intended to limit the invention in any manner, but to merely serve as a general guideline, a typical formulation for a nutritional bar is described in Table 4.

TABLE 4

| Nutritional Bar Formulation | |
| --- | --- |
| Ingredient | Percent Formulation |
| Maltitol | 24 |
| Rolled oats | 21.5 |
| rice crisps | 20.5 |
| soy protein isolate | 5.5 |
| High oleic safflower oil | 4.5 |
| vitamin/mineral premix | 4.15 |
| Flax oil | 3.5 |
| Fructose | 3.2 |
| Glycerin | 2 |
| Whey protein isolate | 2 |
| almonds | 2 |

TABLE 4-continued

| Nutritional Bar Formulation | |
| --- | --- |
| Ingredient | Percent Formulation |
| modified starch | 2 |
| calcium caseinate | 1.5 |
| polydextrose | 1.4 |
| soy polysaccharide | 1 |
| water | 0.8 |
| Corn oil | 0.54 |
| soy lecithin | 0.45 |
| vanilla flavoring | 0.2 |

The typically caloric distribution of a nutritional bar utilizing the ingredient percent of Table 4 is about 15% of the total calories as protein, about 25% of the total calories as fat and about 60% of the total calories as carbohydrate.

The nutritional bar composition is manufactured using cold extrusion technology as is known in the art. To prepare such compositions, typically all of the powdered components will be dry blended together. Such constituents typically include the proteins, vitamin premixes, certain carbohydrates, etc. The fat soluble components are then blended together and mixed with the powdered premix above. Finally any liquid components are then mixed into the composition, forming a plastic like composition or dough.

The process above is intended to give a plastic mass which can then be shaped, without further physical or chemical changes occurring, by the procedure known as cold forming or extrusion. In this process, the plastic mass is forced at relatively low pressure through a die which confers the desired shape and the resultant exudate is then cut off at an appropriate position to give products of the desired weight.

The mass may, for example, be forced through a die of small cross-section to form a ribbon, which is carried on a belt moving at a predetermined speed under a guillotine type cutter which operates at regular intervals. The cutter, in this case, generally consists of a sharpened blade so adjusted that it cuts through the ribbon but not the underlying belt, but may also consist of a wire. In both cases, the principle is the same; the cutting process occurs at intervals that permit the moving ribbon to be cut into pieces of equivalent weight and dimensions. Generally, this is achieved by timing the cutting strokes and maintaining belt speed at an appropriate level, but there also exist computer controlled versions of this mechanism which offer greater versatility. Alternatively, the mass may be forced through a die of large cross-section and then cut at die level into slices by an oscillating knife or wire, which drop onto a moving belt and are thus transported away. The mass may also be extruded as a sheet, which is then cut with a stamp type cutter into shapes that are appropriate, such as a cookie type cutter. Finally, the mass may also be forced into chambers on a rotary die equipped with an eccentric cam that forces the thus-formed material out of the chamber at a certain point in a rotation of the cylindrical die.

After shaping, the formed product is moved by a transfer belt or other type of material conveyor to an area where it may be further processed or simply packaged. In general, a nutritional bar of the type described would be enrobed (coated) in a material that may be chocolate, a compound chocolate coating, or some other type of coating material. In all such cases, the coating material consists of a fat that is solid at room temperature, but that is liquid at temperature in excess of e.g. 31° C., together with other materials that confer the organoleptic attributes. The coating is thus applied to the bar while molten, by permitting the bar to pass through a falling curtain of liquid coating, at the same time passing over a plate or rollers which permit coating to be applied to the under surface of the bar, and excess coating is blown off by means of air jets. Finally, the enrobed bar passes through a cooling tunnel where refrigerated air currents remove heat and cause the coating to solidify.

Experiment I

A study was performed to determine whether formulas rich in MUFA and omega-3 PUFA can improve glucose control and insulin sensitivity, and vascular function in an established animal model of NIDDM/insulin resistance.

Male mice (ob/ob), 6-7 weeks of age and about 40 g body weight were purchased from Jackson Laboratory (Bar Harbor, Me.). These animals were typically insulin resistant and had elevated plasma glucose levels. Mice were housed 5 per cage in microisolator cages with free access to food and water. The animals were acclimated to the laboratory facility for one week then randomized based on postprandial glucose level and body weight to one of the four dietary treatments. The natural oil combinations used to form the fatty acid blends of each dietary treatment are set forth in Table 5

TABLE 5

Experimental Oil Blends[a]

| Group 1 (Control) | Group 2 (Linolenic Acid) | Group 3 (EPA) | Group 4 (DHA) |
|---|---|---|---|
| 10% Canola Oil | 39% Flaxseed Oil | 58% Sardine Oil | 65% Tuna Oil |
| 85% High Oleic Safflower Oil | 50% High Oleic Safflower Oil | 11% High Oleic Safflower Oil | 21% Safflower Oil |
| 5% lecithin | 6% Corn Oil | 26% Safflower Oil | 9% Sardine Oil |
|  | 5% lecithin | 5% lecithin | 5% lecithin |

[a]All percentages are based on weight of total lipid.

The omega-3, omega-6, and omega-9 fatty acid compositions and relative ratios of each oil blend described in Table 5 above are set forth in Table 6 below.

TABLE 6

Fatty Acid Content and Ratios

| Fatty Acid | Group 1 (Control) | Group 2 (Linolenic Acid) | Group 3 (EPA) | Group 4 (DHA) |
|---|---|---|---|---|
| Saturated (%)[a] | 6.8 | 9.2 | 13.5 | 21.9 |
| Omega-9 Total (%) | 74.7 | 48.4 | 18.8 | 18.1 |
| Oleic (C18: 1n-9) | 74 | 48.4 | 18.8 | 16.8 |
| Omega-6 Total (%) | 16.98 | 17.99 | 24.76 | 21.0 |
| Linoleic (C18: 2n-6) | 16.98 | 17.99 | 23.77 | 18.57 |
| Arachidonic (C20: 4n-6) | — | — | 0.79 | 1.26 |
| Omega-3 Total (%) | 1.25 | 24.6 | 35.88 | 34.37 |
| Alpha-Linonenic (C18: 3n-3) | 1.25 | 24.6 | 0.75 | 0.75 |
| Stearidonic (C18: 4n-3) | — | — | 2.25 | 1.17 |
| Eicosapentaenoic (C20: 5n-3) | — | — | 20.85 | 9.02 |
| Docosapentaenoic (C22: 5n-3) | — | — | 2.02 | 1.43 |
| Docosahexaenoic (C22: 6n-3) | — | — | 9.32 | 21.35 |
| Omega-6/Omega-3 | 47.95 | 0.73 | 0.69 | 0.61 |
| Omega-9/Omega-3 | 57.75 | 2.03 | 0.46 | 0.44 |

[a]All percentages are based on weight of total lipid.

A modified Glucerna® OS (Ross Products Division, Abbott Laboratories, Columbus, Ohio) composition was used as the base formula for the study and the experimental formulas were prepared in 8 oz. cans. Glucerna OS was modified by increasing the amount of fat while decreasing the amount of carbohydrate. The protein content remained the same. The composition of each experimental diet is listed in Table 7 below. The liquid formulas used were isocaloric and isonitrogenous, and differed only in lipid blends described above.

TABLE 7

Diet Composition

| Macronutrient | Group 1 (Control) | Group 2 (Linolenic Acid) | Group 3 (EPA) | Group 4 (DHA) | Glucerna® OS[a] |
|---|---|---|---|---|---|
| Protein, % kcal | 18 | 18 | 18 | 18 | 18 |
| Carbohydrate, % kcal | 39 | 37 | 39 | 39 | 37 |
| Fat, % kcal | 43 | 45 | 43 | 43 | 45 |
| SFA, % kcal | 3 | 3 | 5 | 8 | 3 |
| MUFA, % kcal | 31 | 22 | 11 | 9 | 30 |
| PUFA, % kcal | 8 | 20 | 27 | 25 | 7 |

[a]Glucerna® OS lipid system consists of 85% high oleic safflower oil, 10% canola oil and 5% soy lecithin The three high omega-3 diets, (Groups 2, 3, and 4) contained similar ratios of omega-6 to omega-3 fatty acids, but Group 2 differed from Groups 3 and 4 in omega-9 to omega-3 ratio. Groups 3 and 4 also contained relatively high levels of eicosapentaenoic acid and docosahexaenoic acid, and relatively low levels of alpha-linolenic acid compared to Group 2. The final fatty acid compositions were verified by gas chromatography using a HP Model 5890 series II plus gas chromatograph (Hewlett-Packard, Avondale, Pa.) with an Omegawax 320 fused silica capillary column (0.32 mm×30 m×0.25 μm; Supelco, Bellefonte, Pa.).

A total of 60 mice were assigned to the four experimental groups (n=15 mice/group). The mice consumed one of the experimental diets described above and water, ad libitum, as liquid formula diets. The liquid formula diet was provided to the animals through graduated glass drinking bottles. A fresh can of each experimental liquid formula diet was provided for each cage one time per day. Any remaining liquid formula diet from the previous feeding was measured to determine the 24-hour intake per cage. The total amount of liquid formula diet consumed per mouse was determined by dividing the total amount consumed in 24 hours by the total number of mice per cage. This feeding regimen continued throughout the study period. A fifth group of 15 age-matched mice consuming solid chow served as controls for a separate study running concurrently was used as a reference group for comparison of food intake and growth rate.

After four weeks of consuming the experimental diets, free fatty acids and triglycerides were measured, and meal- or insulin-tolerance tests were performed. Free fatty acids and triglycerides were measured by ELISA (ALPCO Diagnostics, Windham, N.H.). Free fatty acid and triglyceride levels after 28 days of consuming the experimental diets are shown in Table 8. Fatty acid levels for the EPA (group 3) and DHA (group 4) groups are significantly different than the control group 1 (P<0.05) and the fatty acid level of the linolenic acid group 2 is less than that measured for the control group.

TABLE 8

Free Fatty Acid and Triglyceride Levels After 28 Days

| Lipid System | Free Fatty Acid (mmol/L)[a] | Triglycerides (mg/dL)[a] |
|---|---|---|
| Group 1 (Control) | 1.37 ± 0.13 | 245 ± 35 |
| Group 2 (Linolenic Acid) | 1.10 ± 0.11 | 135 ± 6[b] |

TABLE 8-continued

Free Fatty Acid and Triglyceride Levels After 28 Days

| Lipid System | Free Fatty Acid (mmol/L)[a] | Triglycerides (mg/dL)[a] |
|---|---|---|
| Group 3 (EPA) | 0.95 ± 0.05[b] | 154 ± 14[b] |
| Group 4 (DHA) | 0.90 ± 0.11[b] | 157 ± 12[b] |

[a]Values are means ± SE.
[b]P < 0.05 vs Group 1.

Triglyceride levels for the linolenic, EPA, and DHA groups (groups 2, 3 and 4, respectively) are significantly different from the control group 1 (P<0.05). As can be readily seen the fatty acid blends of the present invention reduce fatty acid and triglyceride levels.

Meal tolerance tests ("MTT") were performed in n=10 mice/group to assess postprandial glucose metabolism during the end of the fourth week. The animals were first fasted for three hours, then an initial baseline blood sample was taken for glucose analysis. The animals were then gavaged with the MTT formula and additional samples were taken at 15, 30, 60, and 120 minutes post gavage (samples obtained ±5 minutes from these time points are not included in the analyses). The MTT formula consisted of Ensure Plus® Vanilla (Ross Products Division, Abbott Laboratories, Abbott Park, Ill.). The dose of MTT formula given was based on body weight and calculated to provide 1.5 grams of carbohydrate per kilogram (based on total carbohydrates as labeled on the package, which did not take into account indigestible or unavailable carbohydrate).

FIG. 1 is a bar graph of the area under curve for the MTT blood glucose results adjusted to baseline after 4 weeks of diet treatment. The area under curves fit to the data (after the data was adjusted to baseline) are 16,676±1753 for Group 1 (Control MUFA); 10,532±1400 for Group 2 (Linolenic acid); 9,009±1258 for Group 3 (EPA); and 7,867±38 for Group 4 (DHA). Groups 2, 3 and 4 all reach statistical significance at P<0.05 when compared to Control Group 1. It can be readily seen, each group containing omega-3 fatty acids had reduced glucose response after a standard mixed meal.

Insulin tolerance tests ("ITT") were performed in the remainder of mice in each diet group, i.e., n=5 mice/group, during the end of the fourth week. Note that the ITT mice did not undergo MTT and vice versa. The animals were first fasted for three hours, then an initial baseline blood sample was taken. The animals were then injected with insulin intraperitoneally (2 U/kg body weight) and additional blood samples were taken at 15, 30, 60, and 120 minutes post-injection (samples obtained ±5 minutes from these time points are not included in the analyses).

Figure 2:
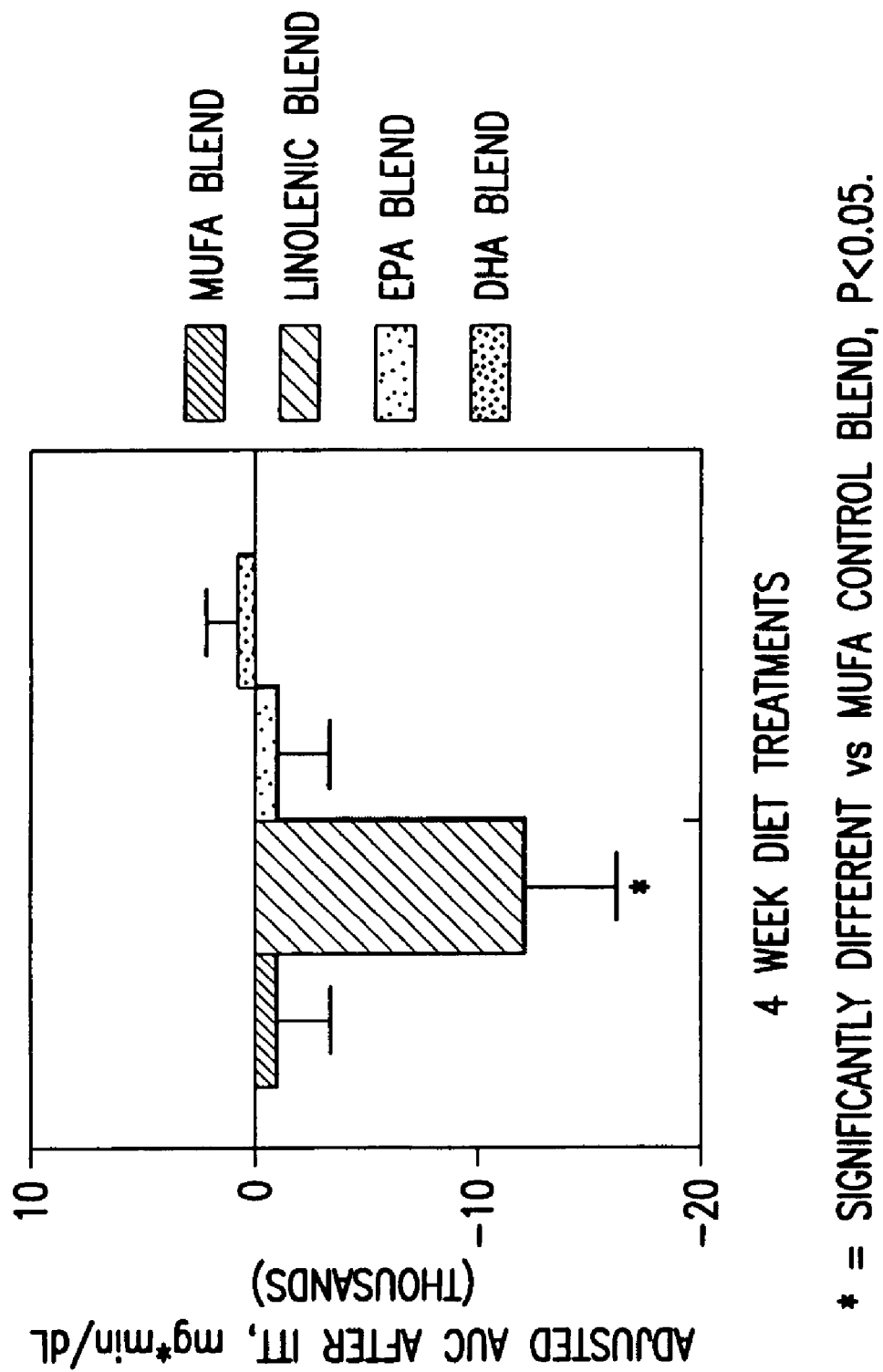
FIG. 2 is an area under the curve bar graph of the Insulin Tolerance Test blood glucose results after 4 weeks of diet treatment after the data was adjusted to baseline. Group 1 Control MUFA blend; Group 2 Linolenic blend; Group 3 EPA blend; and Group 4 DHA blend.

FIG. 2 is a bar graph of the area under the curve for the ITT blood glucose results adjusted to baseline after 4 weeks of diet treatment. The area under curves fit to the data (after the data was adjusted to baseline) are −975±2,435 for Group 1 (Control MUFA); −12,162±4,135 for Group 2 (Linolenic acid); −1,071±2,271 for Group 3 (EPA); and 799±1,368 for Group 4 (DHA). Group 2 is significantly different at P<0.05 when compared to control Group 1. As can be readily seen, only group 2 diabetic mice, which were provided alpha-linolenic acid, demonstrated enhanced insulin sensitivity.

Experiment II

A second study was performed to determine whether dietary intervention with mono-unsaturated fatty acid rich formulas and mono-unsaturated fatty acid rich formulas supplemented with omega-3 PUFAs can improve vascular function in a mouse model of non-insulin dependent diabetes. The capacity of the endothelium-dependent vasoactive agent, carbachol, to induce relaxation in isolated aortic rings was determined. Six groups of male ob/ob mice and their lean-littermates were fed experimental diets for four weeks. The mice were kept in the same manner as described in Experiment I above. For comparison purposes, a group of ob/ob mice and a group of their lean-littermates were fed a standard chow diet. As in Experiment 1, Glucerna® OS (Ross Products Division, Abbott Laboratories, Columbus, Ohio) composition was used as the base formula for the study and the experimental formulas were prepared in 8 oz. cans. Glucerna® OS was modified by increasing the amount of fat and incorporating the lipid systems listed in Table 9.

TABLE 9

Vascular Function Study Group Lipid Systems

| Group 1 (ob/b Chow) (ob/ob; n = 6) | Group 2 (lean Chow) (lean; n = 6) | Group 3 (b/ob MUFA) (ob/ob; n = 7) | Group 4 (Linolenic Acid) (ob/ob; n = 6) | Group 5 (EPA) (ob/ob; n = 6) | Group 6 (lean MUFA) (lean; n = 5) |
|---|---|---|---|---|---|
| Standard Chow | Standard Chow | 10% Canola Oil | 39% Flaxseed Oil | 58% Sardine Oil | 10% Canola Oil |
| | | 85% High Oleic Safflower Oil 5% lecithin | 50% High Oleic Safflower Oil 6% Corn Oil 5% lecithin | 11% High Oleic Safflower Oil 26% Safflower Oil 5% lecithin | 85% High Oleic Safflower Oil 5% lecithin |

After the four week feeding regimen, each animal was anesthetized and the thoracic aorta was rapidly removed and immediately transferred into a modified Krebs' solution containing: NaCl 120 mmol/L; KCl 4.7 mmol/L; $KH_2PO_4$ 1.2 mmol/L; $MgSO_4$ 1.5 mmol/L, $CaCl_2$ 2.5 mmol/L, dextrose 11 mmol/L; and $NaHCO_3$ 20 mmol/L). Under 2× magnification the aortas were cleared of fat and connective tissue and arterial segments 1-2 mm wide were removed with special care to preserve endothelium integrity. The arterial segments were then suspended vertically under 0.5 g of resting tension between two wire hooks in 10 ml organ baths containing the same modified Krebs' solution at 37° C. The tissues were equilibrated with 95% $O_2$ and 5% $CO_2$ (pH 7.4 at 37 C) for 60-90 minutes with the tissue being rinsed at 10 minute intervals. One hook was fixed to the support and the other was connected to an isometric force transducer (Model FT03, Grass Instruments, RI). Changes in isometric tension were continuously monitored on a Grass physiograph (Model 7D, Grass Instruments, RI) and recorded on a PONEMAH data acquisition system (Gould Instrument Systems, OH).

In order to produce endothelium-dependent or endothelium-independent relaxation, the aortic rings were precontracted with phenylephrine ($10^{-5}$ M) and cumulative concentration-effect curves to carbachol were constructed. The agonist concentrations were added in half log molar increments allowing time for the effect to plateau between additions. A carbachol curve was constructed for concentrations between $10^{-9}$ to $4.5 \times 10^{-5}$ M. After construction of the carbachol curve, the aortic rings were allowed to return to basal tone by rinsing every 10 minutes for 60 minutes. Each constriction induced by phenylephrine was used as the internal standard for calculation of carbachol-induced relaxation as a percentage of the phenylephrine-induced precontraction. Aortic rings that exhibited less than 35% vasorelaxation of carbachol, which is indicative of a damaged vascular endothelium, were eliminated from the analysis. From each arterial segment, the actual maximal relaxation ($E_{max}$) was determined and the concentration of the agonist that produced 50% of the maximal effect ($EC_{50}$) was calculated by non-linear regression curve fitting (GraphPad Prism, San Diego, Calif.) and reported as the positive logarithm of the $EC_{50}$ ($pEC_{50}$). The mean $E_{max}$ and $pEC_{50}$ data for each animal treatment group are shown in Table 10. Statistical differences among groups were determined by ANOVA with a post-hoc Newman-Keuls or unpaired Student's t-test.

Figure 3:
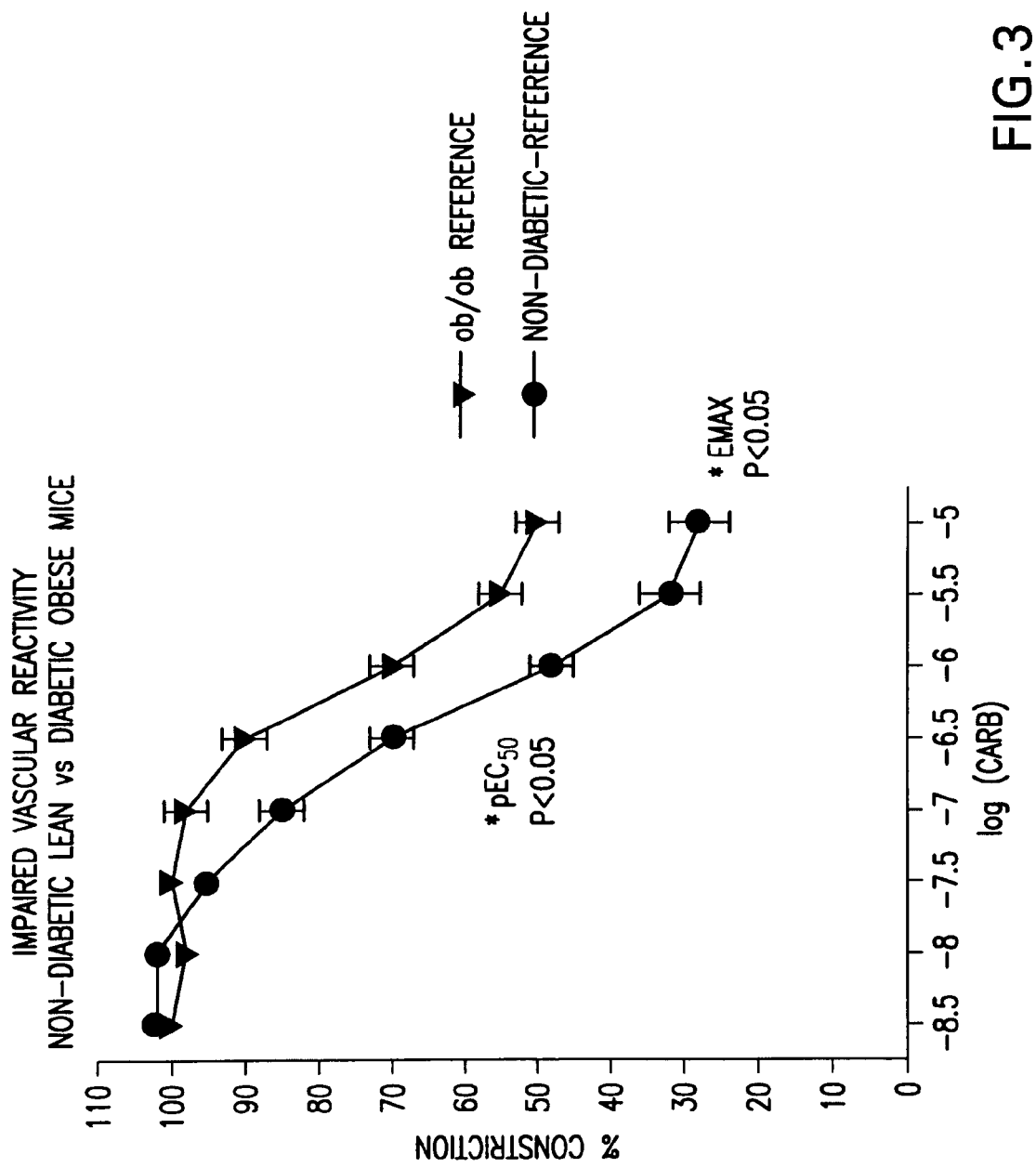
FIG. 3 is a vascular responses graph comparing percent constriction vs carbachol concentration. Group1 Ob/ob Chow reference (▲); Group 2 lean chow non-diabetic reference (●).
Figure 4:
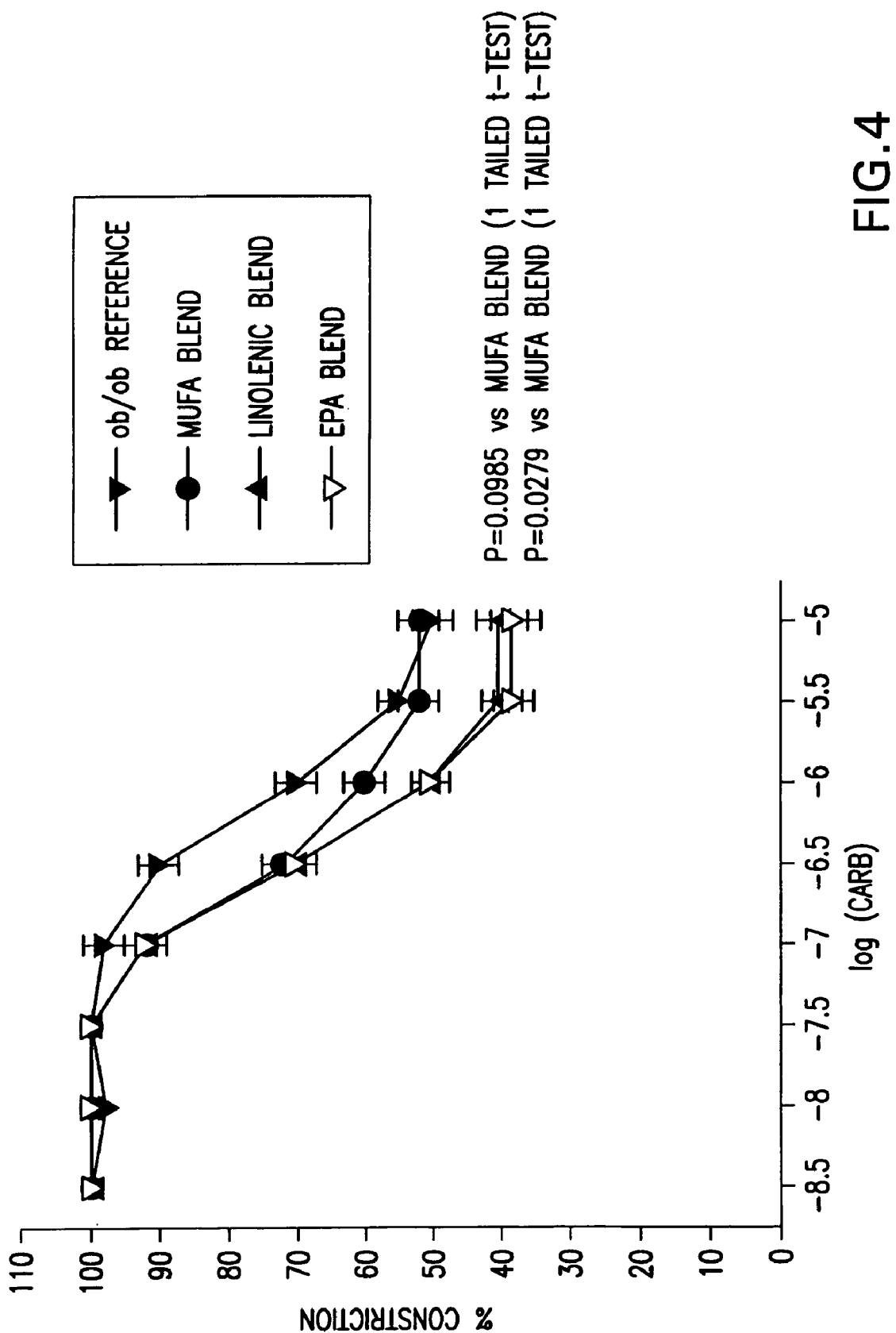
FIG. 4 is a vascular responses graph comparing percent constriction vs carbachol concentration. Group1 Ob/ob Chow reference (black ▲); Group 3 ob/ob control MUFA blend (blue ●); Group 4 ob/ob linolenic blend (yellow ▲); Group 5 ob/ob EPA blend (green ▲).

As can be readily seen from the values in Table 10, Group 2 (non-diabetic lean-standard chow) aortic tissues achieved a greater pEC50 and $E_{max}$ values than Group 1 (ob/ob—standard chow) aortic tissue, as was expected. FIGS. 3 and 4 describe this data by graphing the data as percent constriction versus carbachol concentration. FIG. 3 graphs the data from the chow feed animals, Group 1 and 2, which serve as reference diets for the ob/ob diabetic obese mice model.

TABLE 10

Vasoreactivity Response in Aortic Rings

| Treatment Group | $pEC_{50}$ Carbachol[a] | $E_{max}$[a] |
|---|---|---|
| Group 1 (ob/ob Chow) | $-5.59 \pm 0.08$[b] | $51.9 \pm 5.1$ |
| Group 2 (lean Chow) | $-5.94 \pm 0.10$[c] | $70.7 \pm 6.2$[c] |
| Group 3 (ob/ob MUFA) | $-6.01 \pm 0.07$[c] | $50.6 \pm 3.7$ |
| Group 4 (linolenic) | $-5.99 \pm 0.08$[c] | $59.5 \pm 4.8$[d] |
| Group 5 (EPA) | $-5.95 \pm 0.06$[c] | $64.2 \pm 5.8$[e] |
| Group 6 (lean MUFA) | $-6.15 \pm 0.12$ | $60.1 \pm 7.7$ |

[a]Values are means ± SE.
[b]$P < 0.05$ vs. Group 6.
[c]$P < 0.05$ vs. Group 1.
[d]$P = 0.0985$ vs Group 3 by one tailed t-test.
[e]$P = 0.0279$ vs Group 3 by one tailed t-test.

In addition, animals consuming liquid formula diets with and without n-3 fatty acids (Group 3 ob/ob—Control MUFA formula, Group 4 ob/ob—formula with linolenic acid, Group 5 ob/ob—formula with EPA) also showed significant improvements in vasorelaxant responses when compared to the reference Group 1 animals consuming standard chow. In addition, the pEC50 for ob/ob animals consuming the formula diets were not different compared to the non-diabetic lean-standard chow (Group 2). There was no significant improvement in $E_{max}$ in tissues from animals consuming Control formula with no n-3 PUFA (Group 3), however, tissues from animals consuming formulas containing C18:3n-3 or EPA were improved compared to the Control formula (P=0.0985, Group 4 vs Group 3 by 1-tailed t-test; and P=0.0279, Group 5 vs Group 3 by 1-tailed t-test). The $E_{max}$ for ob/ob animals consuming the n-3 formula diets (Group 4 and Group 5) were not different compared to the non-diabetic lean-standard chow (Group 2). FIG. 4 graphically depicts the experimental variable data, group 4 and 5, compared to the ob/ob chow reference group 1 and the ob/ob MUFA control group 3.

As discussed above, a nutritional product that improves the glucose tolerance of a glucose intolerant individual, improves the insulin sensitivity of an insulin resistant individual, or reduces the risk of vascular disease in an individual at risk for vascular disease would be of great benefit to such individuals. As these studies demonstrate, a lipid system comprising omega-3, omega-6, and omega-9 fatty acids in the specified relative amounts provides these benefits. As demonstrated by these studies, the above described lipid system improves the glucose tolerance of a glucose intolerant individual, improves the insulin sensitivity of an insulin resistant individual, and reduces the risk of vascular disease in an individual at risk for vascular disease.

While various embodiments are presented above, variations and modifications of the disclosed embodiments may occur to those skilled in the art to which the claimed invention pertains. The embodiments described herein are examples only. The disclosure may enable those skilled in the art to make and use embodiments having alternative elements that likewise correspond to the elements of the invention recited in the claims. The intended scope of the claims may thus include other embodiments that do not differ or that insubstantially differ from the literal language of the claims.

What is claimed is:

1. A lipid system comprising naturally occurring oils comprising alpha-linolenic acid (C18:3n-3), omega-6 fatty acids, and omega-9 fatty acids wherein
   the ratio of said omega-6 fatty acids to said alpha-linolenic acid (C18:3n-3) is from about 0.25:1 to about 3:1, and
   the ratio of said omega-9 fatty acids to said alpha-linolenic acid (C18:3n-3) is from about 1:1 to about 3:1.

2. The lipid system as defined in claim 1 wherein the ratio of said omega-6 fatty acids to said alpha-linolenic acid (C18:3n-3) is from about 0.3:1 to about 2.5:1.

3. The lipid system as defined in claim 1 further comprising naturally occurring oils comprising saturated fatty acids with more than 12 carbon atoms, wherein said saturated fatty acids are present in an amount less than about 47 gm per 100 gm lipid.

4. The lipid system as defined in claim 1 wherein said omega-6 fatty acid is selected from the group consisting of linoleic acid (C18:2n-6), gamma-linolenic acid (C18:3n-6), eicosadienoic acid (C20:2n-6), arachidonic acid (C20:4n-6), di-homo-gamma-linolenic acid (C20:3n-6), and combinations thereof.

5. The lipid system as defined in claim 1 wherein said omega-9 fatty acid is selected from the group consisting of oleic acid (C18:1n-9), elaidic acid (C18:1n-9), eicosenoic acid (C20:1n-9), erucic acid (C22:1 n-9), and nervonic acid (C24:1 n-9), and combinations thereof.

6. The lipid system as defined in claim 1 wherein the naturally occurring oils comprise from about 17 to about 54% alpha-linolenic acid (C18:3n-3), from about 17 to about 21% linoleic acid (C18:2n-6), from about 19 to about 52% oleic acid (C18:1n-9), and less than about 47% saturated fatty acids, based on the total weight of the lipid system.

7. The lipid system as defined in claim 1, wherein the naturally occurring oils comprise from 30 to 90% flaxseed oil, from 0 to 60% high oleic safflower oil, and from 0 to 10% corn oil by weight of the naturally occurring oils.

8. A product comprising the lipid system of claim 1 wherein said product is selected from the group consisting of a liquid nutritional product, a solid nutritional product, a semi-solid nutritional product, a product provided as an emulsion, a nutritional product provided as a powder, and a product provided as a soft gelatin capsule.

9. A method for improving the glucose tolerance of a glucose intolerant individual comprising administering the lipid system of claim 1, wherein the ratio of said omega-6 fatty acids to said alpha-linolenic acid (C18:3n-3) in the lipid system is from about 0.61:1 to about 0.73:1.

10. A method for improving the insulin sensitivity of an insulin resistant individual comprising administering the lipid system of claim 1, wherein the ratio of said omega-6 fatty acids to said alpha-linolenic acid (C18:3n-3) in the lipid system is from about 0.61:1 to about 0.73:1.

11. A method for reducing the risk of vascular disease in an individual at risk for vascular disease comprising administering the lipid system of claim 1, wherein the ratio of said omega-6 fatty acids to said alpha-linolenic acid (C18:3n-3) in the lipid system is from about 0.61:1 to about 0.73:1.

12. A method for providing nutrition to an individual comprising administering the nutritional product of claim 8.

13. A nutritional product comprising:
a lipid system comprising naturally occurring oils comprising alpha-linolenic acid (C18:3n-3), omega-6 fatty acids, and omega-9 fatty acids wherein
the ratio of said omega-6 fatty acids to said alpha-linolenic acid (C18:3n-3) is from about 0.25:1 to about 3:1, and
the ratio of said omega-9 fatty acids to said alpha-linolenic acid (C18:3n-3) is from about 1:1 to about 3:1; and
a protein component providing from about 5 to about 35% of the total caloric content, a carbohydrate component providing from about 10 to about 95% of the total caloric content, and a lipid component providing from about 5 to about 70% of the total caloric content.

14. The nutritional product as defined in claim 13 wherein the ratio of said omega-6 fatty acids to said alpha-linolenic acid (C18:3n-3) is from about 0.3:1 to about 2.5:1.

15. The nutritional product as defined in claim 13 further comprising saturated fatty acids with more than 12 carbon atoms, wherein said saturated fatty acids are present in an amount less than 47 g per 100 g lipid.

16. The nutritional product as defined in claim 13 wherein said omega-6 fatty acid is selected from the group consisting of linoleic acid (C18:2n-6), gamma-linolenic acid (C18:3n-6), eicosadienoic acid (C20:2n-6), arachidonic acid (C20:4n-6), di-homo-gamma-linolenic acid (C20:3n-6), and combinations thereof and wherein said omega-9 fatty acid is selected from the group consisting of oleic acid (C18:1n-9), elaidic acid (C18:1n-9), eicosenoic acid (C20:1n-9), erucic acid (C22:1n-9), and nervonic acid (C24:1n-9), and combinations thereof.

17. The nutritional product as defined in claim 13 comprising from about 17 to about 54% alpha-linolenic acid (C18:3n-3), from about 17 to about 21% linoleic acid (C18:2n-6), from about 19 to about 52% oleic acid (18:1n-9), and less than about 47% saturated fatty acids.

18. The nutritional product as defined in claim 13 comprising from about 30 to about 90% flaxseed oil, from about 0 to about 59% high oleic safflower oil and from about 0 to about 7% corn oil.

19. A method for improving the glucose tolerance of a glucose intolerant individual comprising administering the nutritional product of claim 13.

20. A method for improving the insulin sensitivity of an insulin resistant individual comprising administering the nutritional product of claim 13.

21. A method for reducing the risk of vascular disease in an individual at risk for vascular disease comprising administering the nutritional product of claim 13.

22. A method for providing nutrition to an individual comprising administering the nutritional product of claim 13.

* * * * *